United States Patent [19]

Weis, Jr. et al.

[11] 3,940,803

[45] Mar. 2, 1976

[54] METHOD AND SYSTEM FOR CONTROL OF A POWERED PROSTHETIC DEVICE

[75] Inventors: Edmund B. Weis, Jr.; Craig R. Hassler; John H. Flora, all of Columbus, Ohio

[73] Assignee: Battelle Memorial Institute, Columbus, Ohio

[22] Filed: May 6, 1974

[21] Appl. No.: 467,073

[52] U.S. Cl. .............................................. 3/1.1; 3/1
[51] Int. Cl.² ...................... A61F 1/00; A61F 1/06
[58] Field of Search ...................... 3/1–1.1, 12.–12.7; 128/419 B, 2 S

[56] References Cited
UNITED STATES PATENTS

| | | | |
|---|---|---|---|
| 2,382,403 | 8/1945 | Eberle | 3/12.6 |
| 3,273,559 | 9/1966 | Evans | 128/2 S |
| 3,646,615 | 3/1972 | Ness | 3/1 |

FOREIGN PATENTS OR APPLICATIONS

| | | | |
|---|---|---|---|
| 351,652 | 4/1922 | Germany | 3/1 |

OTHER PUBLICATIONS

"New Results of the Progressive Developments of an Implantable Magnetic Core Antenna for Myoelectric Signal Transmission" by A. Engelhardt et al., IEEE Transactions On Magnets, Vol. MA9-6, No. 2, June 1970, pp. 338–343.

*Primary Examiner*—Ronald L. Frinks
*Attorney, Agent, or Firm*—Stephen L. Peterson; Philip M. Dunson; C. Henry Peterson

[57] ABSTRACT

The present invention is a concept to provide a means of movement control for a powered prosthetic device. An externally detectable article is implanted on a biological site where the exertion of muscle tension will impart a movement of the article. The muscle can be attached to an antagonistic natural muscle or some means of exerting an opposing tension on the natural muscle. The recipient controlled tension in the appropriate muscle moves the externally detectable article and an external detector monitors that movement and generates control signals to the means powering the device in relation to the amount and direction of movement of the implanted article.

8 Claims, 4 Drawing Figures

METHOD AND SYSTEM FOR CONTROL OF A POWERED PROSTHETIC DEVICE

BACKGROUND OF THE INVENTION

The present invention pertains to that field of the art where artificial limbs replace natural limbs that are missing or are surgically removed. Specifically the present invention is a control means for a powered artificial limb.

DESCRIPTION OF THE PRIOR ART

Artificial limbs are generally classified in two categories; passive or powered. A passive artificial limb moves by the exertion of remaining muscles and any specific function such a limb might have over simple motion such as grasping is also controlled by remaining muscles.

A second type of artificial limb is powered by some source of energy and its motion and specific functions are generated by a power source in or associated with the artificial member. The application of power to the limb must be under the control of the recipient and several prior art references teach such control means.

One body of prior art can be classified as electromyogram devices where electrodes on the skin of the recipient monitor the electrical activity of the adjacent muscle and translate that electrical activity to a logic system where it is transformed into control signals for the means powering the artificial limb. Typical of such a system is U.S. Pat. No. 3,418,661, Allison et al., where electrodes attached to two antagonistic muscles receive electromyogram (EMG) signals and those signals are amplified rectified and electronically filtered. The difference between the two signals generates a control signal to an electric motor operating on a closed loop system. The closed loop system receives a force and velocity feedback so as to control the signal to the motor moving the artificial member. Similarly U.S. Pat. Nos. 3,641,993, Gaardner et al.; 3,491,378, Ioffe et al.; and 3,501,776, Beeker et al., all use electromyogram outputs to generate control signals for a powered prosthetic limb. There are several deficiencies of such control systems the major one being the lack of feedback to the recipient as to the force and effect of the exertion being generated. Additionally the myoelectric signals are electrically noisy and from the standpoint of control there is only a rough relationship between muscle tension and myoelectric output. The result of these inherent shortcomings is that the recipient must undergo significant training in the operation of the device and its operation is the result of learned unnatural exertions of muscle tension.

U.S. Pat. No. 3,609,769, Suzuki et al., teaches a different type of prosthetic control system where the movement of a voluntary muscle activates the power to drive the prosthetic device. This reference teaches specific means to provide a feedback to the recipient so as to provide closed loop control to the powered device.

BRIEF SUMMARY OF THE INVENTION

The present invention is a means of controlling the movement of a powered prosthetic device by internally implanting a detectable article on or adjacent to a muscle attached to a member capable of exerting a tension in opposition to the muscle. The biological site of the placement of the detectable article must be one capable of being moved by the action of a remaining muscle. An external detector monitors the position of the article and generates a signal to the power means in relation to the location of the article. Therefore the recipient can proportionally move the prosthetic limb simply by exerting muscle movement against the resistance of the opposite tension force. In a preferred embodiment the opposing tension would be from the natural antagonist of the antagonistic muscle pair that originally moved the natural limb. In that instance motion of the powered artificial limb would be initiated and controlled by the exertion of the same muscles or muscle remnants in a manner similar to natural muscular control. Where there is only one remaining muscle of the original antagonistic pair then the natural muscle can be attached to an elastic member exerting an opposing tension for a simulation of the missing antagonist.

DETAILED DESCRIPTION OF THE INVENTION

Figure 1:
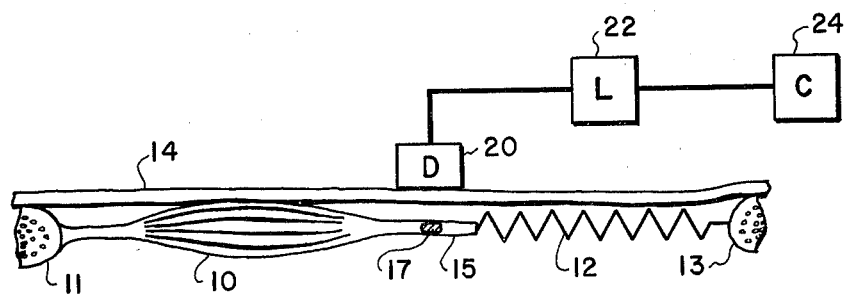
FIG. 1 is a schematic representation of the present invention where the intact muscle is opposed by an elastic member.
Figure 2:
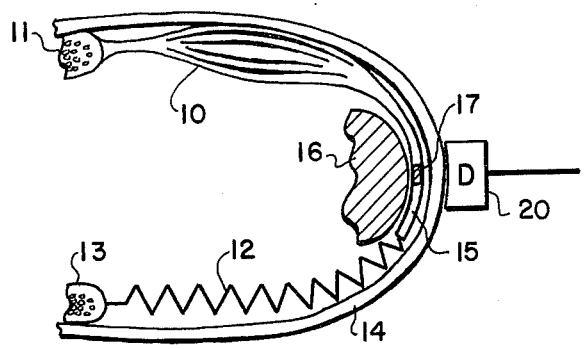
FIG. 2 is a schematic representation of the present invention where the elastic member is not in line with the natural muscle.

FIGS. 1 and 2 show two embodiments of the present invention where a natural muscle 10 fixed to some portion of the skeletal system 11 is attached at its opposite end to an elastic member 12. The elastic member is in turn attached to the skeletal system at point 13 thereby immobilizing the end opposite the end attached to the muscle. The connective member 15 between the muscle 10 and the elastic member 12 has an article 17 attached thereto. The article 17 is of a composition and size so as to be externally detectable by the detector 20 separated from the article 17 by tissue 14. The detector 20 is in turn connected to control 22 and slave means 24 that take the output of the detector 20 in relation to the magnitude and direction of the movement of the article 17 and convert it into the appropriate motion of the powered prosthetic device.

FIG. 2 differs from FIG. 1 solely in the geometric arrangement of the elements. Where it is desired to place the elastic member 12 at a location that is not in line with the natural muscle 10 then the connective member 15 can be curved to the location of the elastic member as long as the connective member is supported. FIG. 2 simply shows a supporting member 16 disposed to retain the connective member in a specific location and allow relative motion between the connective member 15 and the support 16. The support 16 can be comprised of any material capable of supporting the connecting member 15. For example it could be tissue, bone or an artificial support specifically placed for the purpose of supporting the connective member 15. In a preferred embodiment the support would be tissue with the connecting member 15 within a sheath, naturally formed by the body surrounding the connecting member.

Figure 3:
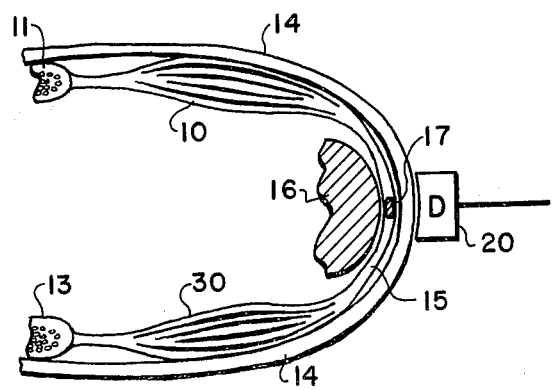
FIG. 3 is a schematic representation of the present invention where two antagonistic muscles are attached to form an antagonistic pair with the detectable article between them.

FIG. 3 shows an embodiment of the invention where the detectable article 17 is attached to a connective member 15 that connects two natural muscles 10 and 30. In this embodiment the recipient of the control means determines the motion of the powered prosthetic device by moving the article 17 with the relative tension of the two natural muscles 10 and 30. In a manner similar to the motion of a normal member the recipient controls the muscle pair like a natural antagonistic muscle pair. Where the tension in the muscle 10 exceeds that of the muscle 30 then the article 17 will move toward muscle 10. Conversely the direction of movement is reversed if the muscle 30 exerts a tension of greater magnitude than that of muscle 10.

Whether the natural muscle 10 exerts a force in opposition to a static tension from an artificial member or an opposing natural muscle the control of the powered prosthetic device is essentially the same.

The natural muscle 10 (or 30) need not be a wholly intact muscle and a muscle remnant is operable as long as there is sufficient control and strength to move the article in relation to the desired movement of the powered prosthetic device. In the embodiments using an artificial static tension means to resist the natural muscle the magnitude of the opposing tension can be set in relation to the strength of the opposing natural muscle or muscle remnant.

The connective member 15 may be a natural tendon or an artificial tendon. Where an artificial tendon is used it must be compatible with the body and be able to move in relation to the surrounding tissue without causing irritation. Several specific artificial tendons are known in the art with biological grade silicone rubber (Silastic) covered Dacron being particularly successful.

Figure 4:
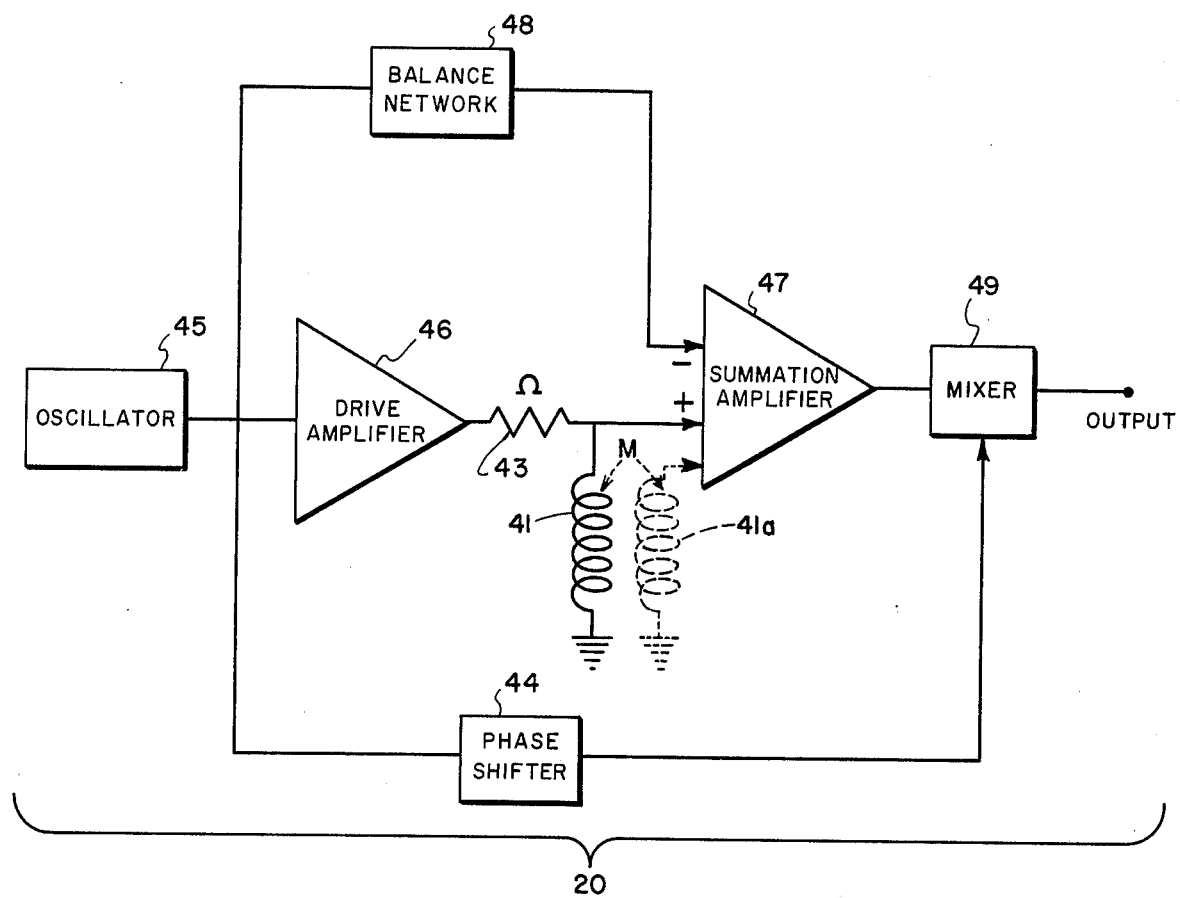
FIG. 4 is an embodiment that externally detects the movement of the implanted article and converts it to a signal that can control the movement of a powered prosthetic device.

FIG. 4 is a specific embodiment of a device capable of converting the magnitude and direction of movement of the article 17 into a control signal for the powered prosthetic device. The detector 20 consists of at least one induction coil 41 which is placed externally adjacent the article 17. The presence of the article 17 in a field produced by the coil 41 will distort the field in relation to the position of the article if the article is of sufficient size and comprised of either an electrically conductive or ferromagnetic or ferrimagnetic material.

When the coil 41 is excited by alternating current a magnetic flux is generated adjacent the coil. If for example a ferromagnetic material is within the magnetic field the alternating flux density is increased. In addition electromagnetic induction causes current to flow within the ferromagnetic material. Either of the two effects may be used to remotely monitor the position of a ferromagnetic material, i.e., the change in flux density alters the coils inductive reactance and the electromagnetic induction in the article effects the coil's impedance by the reaction of the eddy currents induced in the article with the coil. The use of more than one coil, for example, the coil 41 and the optional dotted-line coil 41a, in FIG. 4, in similar embodiments may utilize mutual inductance coupling between the coils and/or the detection of impedance changes of these coils to monitor the position of the detectable article. The relative amount of the changes in coil inductance and resistance (electrical impedance) and mutual coupling is dependent on several factors; number of coils, coil geometry, excitation frequency and the size and electrical characteristics of the detectable article.

The embodiment shown in FIG. 4 is disposed to change the impedance variations of the coil to corresponding voltage changes. This embodiment utilizes conventional electronic components with no attempt to miniturize the apparatus for actual prosthetic application. The apparatus of this embodiment successfully illustrates that the internal movement of an implanted article can be externally detected and transformed into a corresponding voltage change which would form the input for an electrical system disposed to move the artificial member.

FIG. 4 illustrates an embodiment where the impedance component on an excited coil were translated to a linear voltage change in relation to the position of a metal implant (the detectable article 17). An oscillator 45 is employed to excite three networks: a driver amplifier 46, a balance adjustment network 48, and a phase shifter 44. The driver amplifier 46 energizes the sensing coil 41 through a 50 ohm resistor 43 and the balance network 48 provides a signal voltage identical to the voltage seen across the sensing coil terminals when no metal objects are near the coil. The coil voltage and the balance network voltage are subtracted by the sum amplifier 47 to provide a near zero output voltage when the coil is in air. When the metal article is brought in proximity to the coil, the voltage across the coil changes to provide a corresponding change at the output of the summation amplifier 47.

The summation amplifier output voltage is then applied to the mixer 49, which multiplies it with the output from the phase shifter. Since output voltage from the summation amplifier has the same frequency as the voltage from the phase shifter a d-c voltage is provided at the mixer output. This voltage is proportional to the amplitude of the summation amplifier output multiplied by the cosine of the angle difference between the phase shifter output and the summation amplifier output. Therefore, by adjusting the phase shifter, various components of sensing coil impedance are measured. This technique of mixing a reference signal with the sensing coil voltage is commonly referred to as phase-lock detection. The commercial lock-in amplifier was employed with other fabricated components to measure the impedance components of the coil as a ferromagnetic implant was moved away from the center of the sensing coil.

The present invention was used in the following specific example:

EXAMPLE 1

A ferromagnetic material approximately 1/16 inch in diameter and ½ inch long was implanted in a tendon of a dog with approximately 1/16 inch of tissue between the implant and the sensing coil. A flat sensing coil having distributed windings was used to sense the position of the ferromagnetic implant as it was moved parallel to the plane of the coil. Voltage outputs from the lock-in amplifier were recorded as the ferromagnetic implant was moved along its axis parallel to the plane of the coil. The zero position was taken as the center of the sensing coil. The output show a nearly linear response from the 0.1 to 0.4 inch position and the average noise is estimated to be less than 5 percent. This indicates the potential of accurately sensing the implant position over a range of at least ¼ inch without physical penetration of the skin.

The present invention has been disclosed by specific example and general description and one skilled in the art may devise variations of the invention not specifically described, however, the scope of this invention is defined by the following claims.

We claim:

1. A transcutaneous method of exerting control on a powered prosthetic limb comprising the placement of an externally electromagnetically detectable article on a connective member between two antagonistic muscles with the relative tension on the two muscles determining the position of said article and the position of said article being externally electromagnetically detected and used to control the position of said prosthetic limb in relation to the movement of said article.

2. A transcutaneous method of exerting control on a powered prosthetic limb comprising:
   a. implanting an electromagnetically detectable article on a biological site capable of being moved by the action of a remaining muscle;
   b. externally, electromagnetically sensing the movement of said article; and
   c. generating control signals to the limb's power means in relation to said movement.

3. A transcutanceous system for controlling the motion of a powered prosthetic limb comprising:
   a. an externally, electromagnetically detectable article of a size and shape to be internally placed on a biological site capable of being moved by the action of a remaining muscle; and
   b. electromagnetic detection means externally adjacent said article disposed to generate control signals to the limb's power means in relation to the displacement of said article.

4. The system of claim 3 including a connective member adapted to be connected between a pair of antagonistic muscles.

5. The system of claim 3 where said detection means includes at least one induction coil and the movement of said detectable article alters the flux adjacent said coil.

6. The system of claim 5, including means for monitoring the change in inductive reactance of said coil.

7. The system of claim 5, including means for monitoring the change in coil resistance.

8. The system of claim 5 where said detection means includes at least two inductively coupled coils and said article changes the inductance coupling between said coils in relation to the displacement of said article.

* * * * *